(12) United States Patent
Larsen

(10) Patent No.: US 8,703,453 B2
(45) Date of Patent: Apr. 22, 2014

(54) NON-STERILE FERMENTATION OF BIOETHANOL

(75) Inventor: Jan Larsen, Tommerup (DK)

(73) Assignee: Inbicon A/S, Fredericia (DK)

( * ) Notice: Subject to any disclaimer, the term of this patent is extended or adjusted under 35 U.S.C. 154(b) by 0 days.

(21) Appl. No.: 13/356,664

(22) Filed: Jan. 24, 2012

(65) Prior Publication Data

US 2012/0122174 A1 May 17, 2012

Related U.S. Application Data

(62) Division of application No. 12/808,746, filed as application No. PCT/IB2008/003536 on Dec. 18, 2008, now Pat. No. 8,187,849.

(60) Provisional application No. 61/015,688, filed on Dec. 21, 2007.

(30) Foreign Application Priority Data

Dec. 21, 2007 (DK) .................................. 2007 01862

(51) Int. Cl.
*C12P 7/06* (2006.01)

(52) U.S. Cl.
USPC .......................... 435/161; 435/165; 435/254.2

(58) Field of Classification Search
None
See application file for complete search history.

(56) References Cited

U.S. PATENT DOCUMENTS

| | | | |
|---|---|---|---|
| 4,461,648 A | 7/1984 | Foody | |
| 5,424,417 A | 6/1995 | Torget et al. | |
| 6,409,841 B1 | 6/2002 | Lombard | |
| 7,709,042 B2 | 5/2010 | Foody et al. | |
| 7,754,456 B2 | 7/2010 | Penttila et al. | |
| 7,820,418 B2 | 10/2010 | Karl et al. | |
| 8,123,864 B2 | 2/2012 | Christensen | |
| 8,187,849 B2 | 5/2012 | Larsen et al. | |
| 2006/0177917 A1 | 8/2006 | Warzywoda | |
| 2008/0041366 A1 | 2/2008 | Wahnon | |
| 2008/0073507 A1 | 3/2008 | Bonn et al. | |
| 2008/0145903 A1 | 6/2008 | Holmes et al. | |
| 2009/0056707 A1 | 3/2009 | Foody et al. | |
| 2009/0104157 A1 | 4/2009 | Solomon et al. | |
| 2009/0209009 A1 | 8/2009 | Tolan et al. | |
| 2009/0258404 A1 | 10/2009 | Mikkelsen et al. | |
| 2010/0041119 A1 | 2/2010 | Christensen et al. | |
| 2010/0143988 A1 | 6/2010 | Mikkelsen et al. | |
| 2010/0170504 A1 | 7/2010 | Zhang | |
| 2010/0221819 A1 | 9/2010 | Foody et al. | |
| 2010/0273217 A1 | 10/2010 | Maestracci | |
| 2010/0285556 A1 | 11/2010 | Feldmann | |
| 2011/0171708 A1 | 7/2011 | Larsen et al. | |

FOREIGN PATENT DOCUMENTS

| | | |
|---|---|---|
| WO | WO0160752 A1 | 8/2001 |
| WO | WO 2005118828 A1 * | 12/2005 |
| WO | WO2006032282 A1 | 3/2006 |
| WO | WO 2006050193 A2 * | 5/2006 |
| WO | WO2006056838 A1 | 6/2006 |
| WO | WO2007009463 A1 | 1/2007 |

OTHER PUBLICATIONS

Palmqvist and Hahn-Hagerdal "Fermentation of lignocellulosic hydrolysates: I: inhibition and detoxification." (2000) Bioresource Technology, vol. 74, 17-24.*
Wunsche, "Importance of Bacteriophages in Fermentation Processes." (1989) Acta Biotechnology, vol. 5, 395-419.*
Lee, "Biological conversion of lignocellulosic biomass to ethanol" (1997) Journal of Biotechnology, vol. 56, 1-24.*
H. Klinke et al., "Inhibition of ethanol-producing yeast and bacteria by degradation products produced during pretreatment of biomass," Appl. Microbiol. Biotechnol. (2004) 66:10-26.
C. Martin et al., "A study of three strategies for improving the fermentability of sugarcane bagasse hydrolysates for fuel ethanol production," International Sugar Journal (2007) 109(1297):33.
Sakai et al., "Effect of lignocellulose-derived inhibitors on growth of and ethanol production by growth-arrested *Corynebacterium glutamicum* R," Applied and Environmental Microbiology (2007) 73(7):2349-2353.
D. Schell et al., "Contaminant occurrence, identification and control in a pilot-scale corn fiber to ethanol conversion process," Bioresource Technology (2007) 98: 2942-2948.
N. Mosier et al., "Features of promising technologies for pretreatment of lignocellulosic biomass," Bioresource Technology (2005) 96:673.
Palmqvist E, H Grage, NQ Meinander and B Hahn-Hägerdal (1999). Main and interaction effects of acetic acid, furfural, and p-hydroxybenzoic acid on growth and ethanol productivity of yeasts. Biotechnol. Bioeng. 63: 46-55.

(Continued)

*Primary Examiner* — Jon P Weber
*Assistant Examiner* — Teresa E Knight
(74) *Attorney, Agent, or Firm* — Robert C. Casad, Jr.

(57) ABSTRACT

A range of concentrations exists in which fermentation inhibitors derived from pretreatment of lignocellulosic feed stocks inhibit growth of lactic acid bacteria without affecting fermentive yeast. By optimizing levels of fermentation inhibitors to fall within this range, yeast fermentations of lignocellulosic biomass can be conducted under non-sterile conditions with ethanol yields comparable to those achieved under sterile conditions. Optimised inhibitor levels can be achieved by controlling the water/biomass ratio of a lignocellulosic biomass during and after pretreatment, for example by washing the fiber fraction of a previously pretreated lignocellulosic biomass with a pre-defined amount of fresh water or recycled process solutions. Crude extracts of liquid fraction or process solutions from pretreatment of lignocellulosic biomass can also provide an effective anti-bacterial treatment for first generation starch fermentations.

7 Claims, 13 Drawing Sheets

(56) References Cited

OTHER PUBLICATIONS

Zaldivar J, A Martinez and LO Ingram (1999). Effects of selected aldehydes on the growth and fermentation of ethanologenic *Escherichia coli*. Biotechnol. Bioeng. 65. 24-33.
N. Aziz, et al., "Comparative antibacterial and antifungal effects of some phenolic compounds," Microbios (1998) 374:43.
R. Capasso et al., "Antibacterial polyphenols from olive oil mill waste waters," Journal of Applied Bacteriology (1995) 79:393.
S. Naz et al., "Antibacterial activity directed isolation of compounds from *Onosma hispidum*," Microbiological Research (2006) 161:43.
M. Fernandez et al., "Antibacterial activity of the phenolic acids fractions of *Scrophularia frutescens* and *Scrophularia sambucifolia*," Journal of Ethnopharmacology (1996) 53:11.
M. Mokbel and T. Suganuma, "Antioxidant and antimicrobial activities of the methanol extracts from pummelo (*Citrus grandis* Osbeck) fruit albedo tissues," Eur. Food Res. Technol (2006), 224:39.
Almeida JRM, T Modig, A. Petersson, B. Hähn-Hägerdal, G. Lidén and MF Gorwa-Grauslund (2007). Increased tolerance and conversion . . . Journal of chemical technology and biotechnology 82: 340-349.
Liu ZL.(2006) Genomic adaptation of ethanologenic yeast to biomass conversion inhibitors. Appl Microbiol Biotechnol 73: 27-36.
Skinner K.A. & T.D. Leathers (2004). Bacterial contaminants of fuel ethanol production. J Ind Microbiol Biotechnol, vol. 31, pp. 401-408.
Palmqvist, E. et al., Fermentation of lignocellulosic hydrolysates I: Inhibition and detoxification, Bioresource Technology, 2000, 74(1), 17-24.
Communications in connection with EP 08871113.0 and responses, dated Feb. 27, 2012.
Nilsson et al., Use of dynamic step response for control of fed-batch conversion of lignocellulosic hydrolyzates to ethanol, Journal of Biotechnology 89 (2001)41-53.
Nilsson et al. On-line estimation of sugar concentration for control of fed-batch fermentation of lignocellulosic hydrolyzates by *Saccharomyces cerevisiae*, Bioprocess Bosyst eng 25 (2002) 183-181.
Rivera et al. Lactic acid and biosurfactants production from hydrolyzed distilled grape marc, Process Biochemestry 42 (2007) 1010-1020.
Stenberg et al, the influence of lactic acid formation on the simultaneous saccharification and fermentation (SSF) of softwood to ethanol, Enzyme and Microbial Technology 26 (2000) 71-79.
Taherzadeh et al: Conversion of dilute-acid hydrolyzates of spruce and birch to ethanol by fed-batch fermentation, Bioresource Technology 69 (1999) 59-66.
Taherzadeh et al. On-line control of fed-batch fermentation of dilute-acid hydrolyazates, Biotechnology and bioengineering, vol. 69, No. 3 (2000).
Stenberg et al. Recycling of process streams in ethanol production from softwood based on enzymatic hydrolysis, Applied Biochemistry and Biotechnology, vol. 70-72, 1998, 697-708.
Palmqvist et al. Fermentation of lignocellulosic hydrolysates. II: inhibitors and mechanisms in inhibition, Bioresourse Technology, 74 (2000) 25-33.
International search report and written opinion for PCT/IB2008/003536 and IPER, dated Jul. 20, 2009.
Abatzoglou et al. Phenomenological kintetics of complex systems: the development of a generalized severity parameter and its application to lignocellulosics fractionation, Chemical engineering science, vol. 47, No. 5 pp. 1109-1122, 1992.
Schell et al: A bioethanol process development unit: Initial operating experiences and results with a corn fiber feedstock, Bioresource Technology 91 (2004) 179-188.
Palmqvist et al: Design and operation of bench-scale pro cess development unit for the production of ethanol from lignosellulosics, Bioresourse Technology vol. 58, No. 2, Nov. 1, 1996, pp. 171-179.
Kadar et al. Ethanol fermentation of various pretreated and hydrolyzes substrates at low initial pH, Applied Biochemistry and Biotechnology, vol. 137, Apr. 1, 2007, pp. 847-857.
Carlos Martin et al: Investigation of cellulose convertibility and ethanolic fermentation of sugarcane bagasse pretreated by wet oxidation and steam explosion, Journal of Chemical Technology and Biotehchnology, vpl 81, No. 10, pp. 1669-1677.
Müller-Merbach et al: Inactivation of bacteriophages by thermal and high-pressure treatment, International Dairy Journal 15 (2005) 777-784.

\* cited by examiner

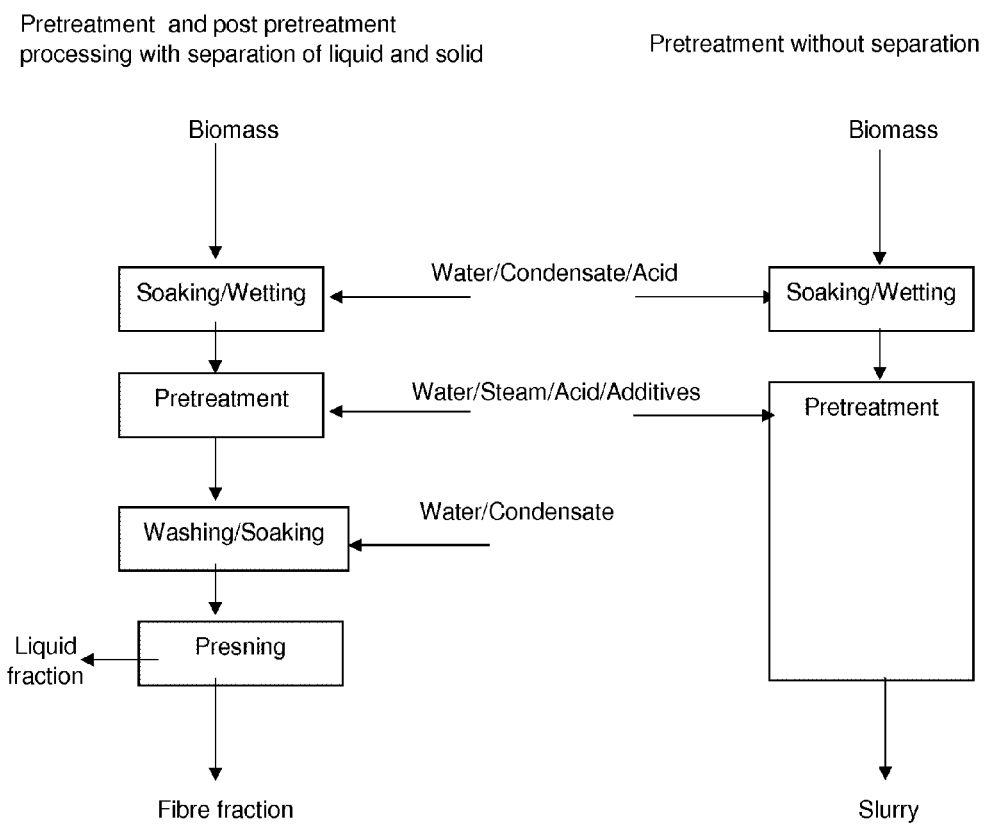
FIG. 1. Schematic illustration of process steps in pretreatment of lignocellulosic biomass.

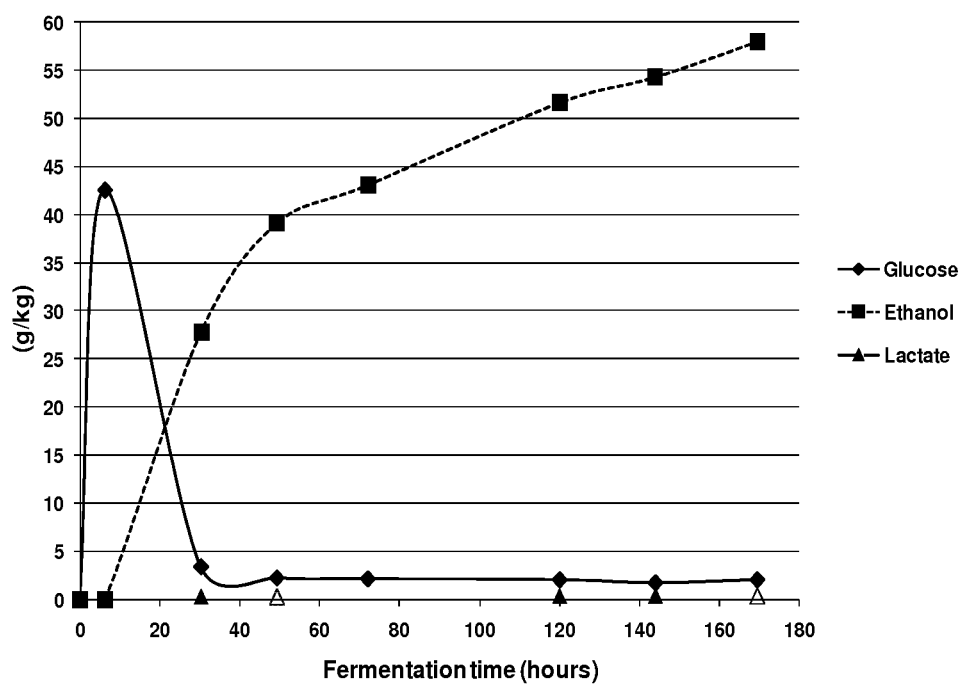
FIG. 2. Non-sterile pre-hydrolysis and SSF of pretreated wheat straw having a water/biomass ratio of 5:1.

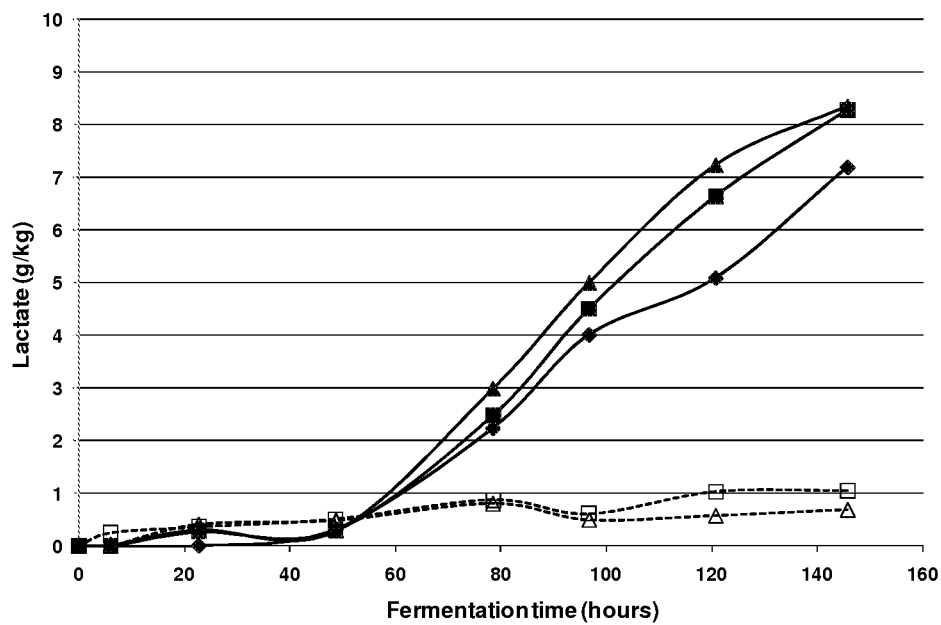
FIG. 3. Non-sterile pre-hydrolysis and SSF of pretreated wheat straw having a water/biomass ratio of 5:1 (dotted curves) compared with 11:1 (full line curves).

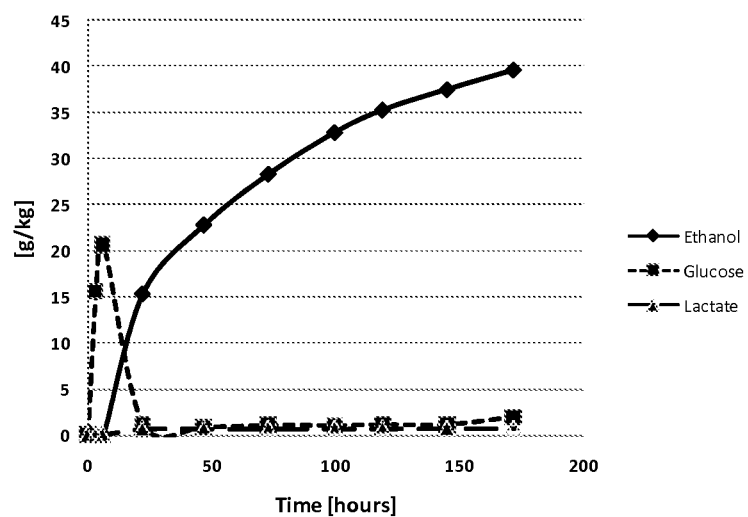
FIG. 4. Non-sterile pre-hydrolysis and SSF of pretreated bagasse having water/biomass ratio 5:1.

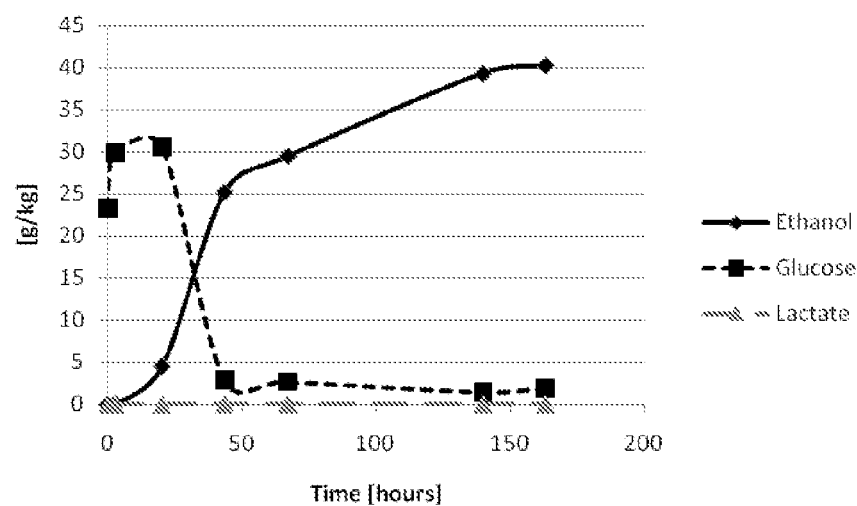
FIG. 5. Non-sterile pre-hydrolysis and SSF of pretreated corn stover having water/biomass ratio 5:1.

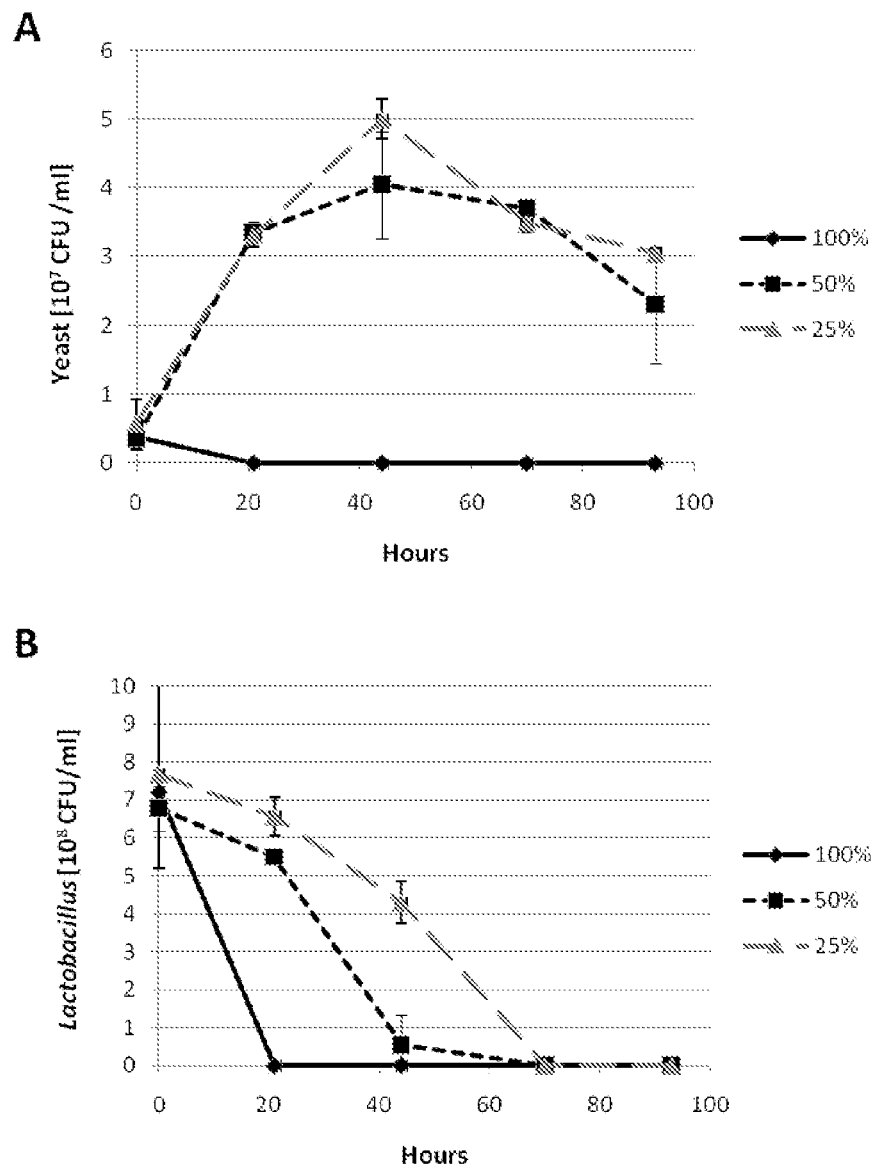
FIG. 6. Effects of varying concentrations of liquid fraction (%) on yeast CFU (A) and *Lactobacillus* CFU (B) over the course of glucose fermentation.

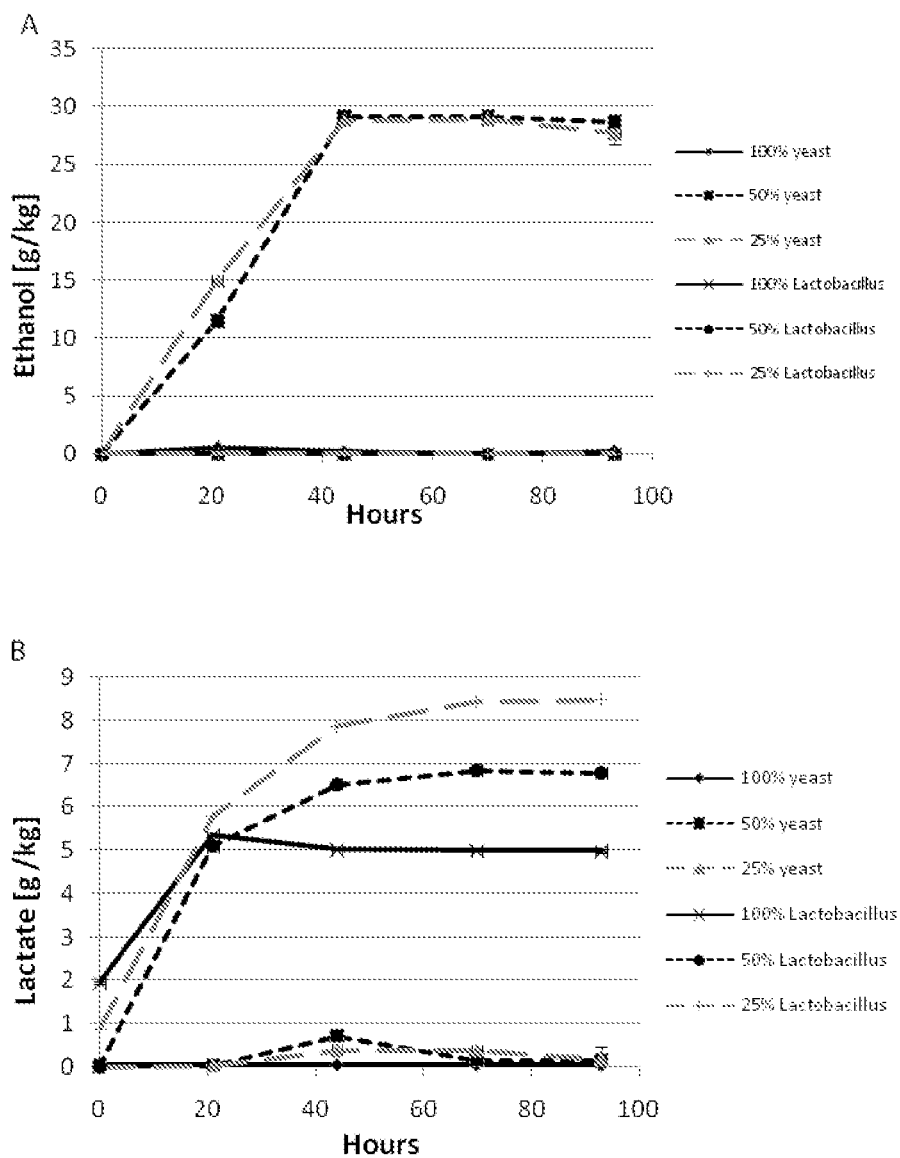
FIG. 7. Effects of varying concentrations of liquid fraction (%) on ethanol (A) and lactate (B) concentration over the course of glucose fermentation by yeast and *Lactobacillus*.

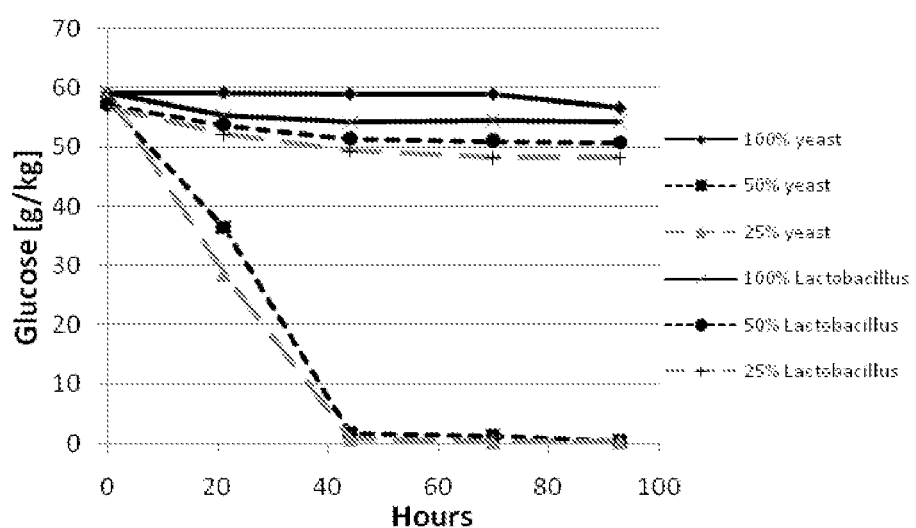
FIG. 8. Effects of varying concentrations of liquid fraction (%) on glucose consumption by yeast and *Lactobacillus* during glucose fermentation.

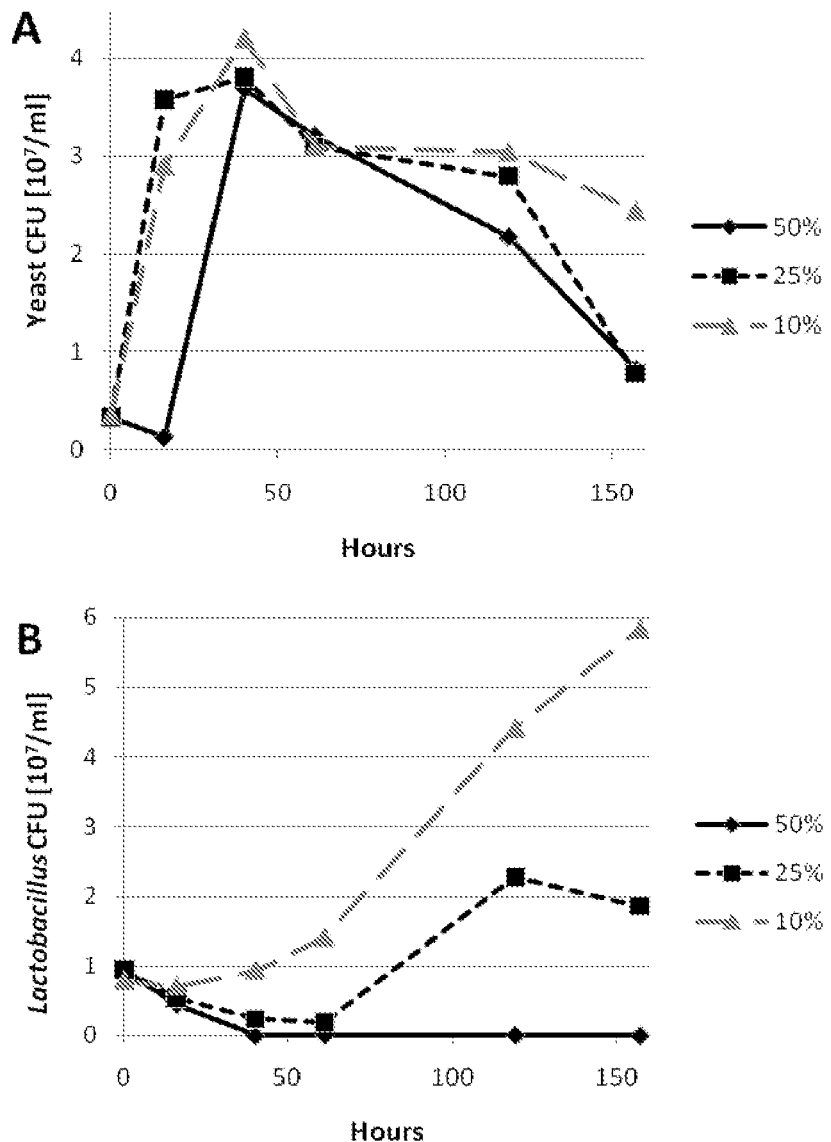
FIG. 9. Effects of varying concentrations of liquid fraction (%) on yeast (A) and *Lactobacillus* (B) cell number during SSF of pretreated wheat straw.

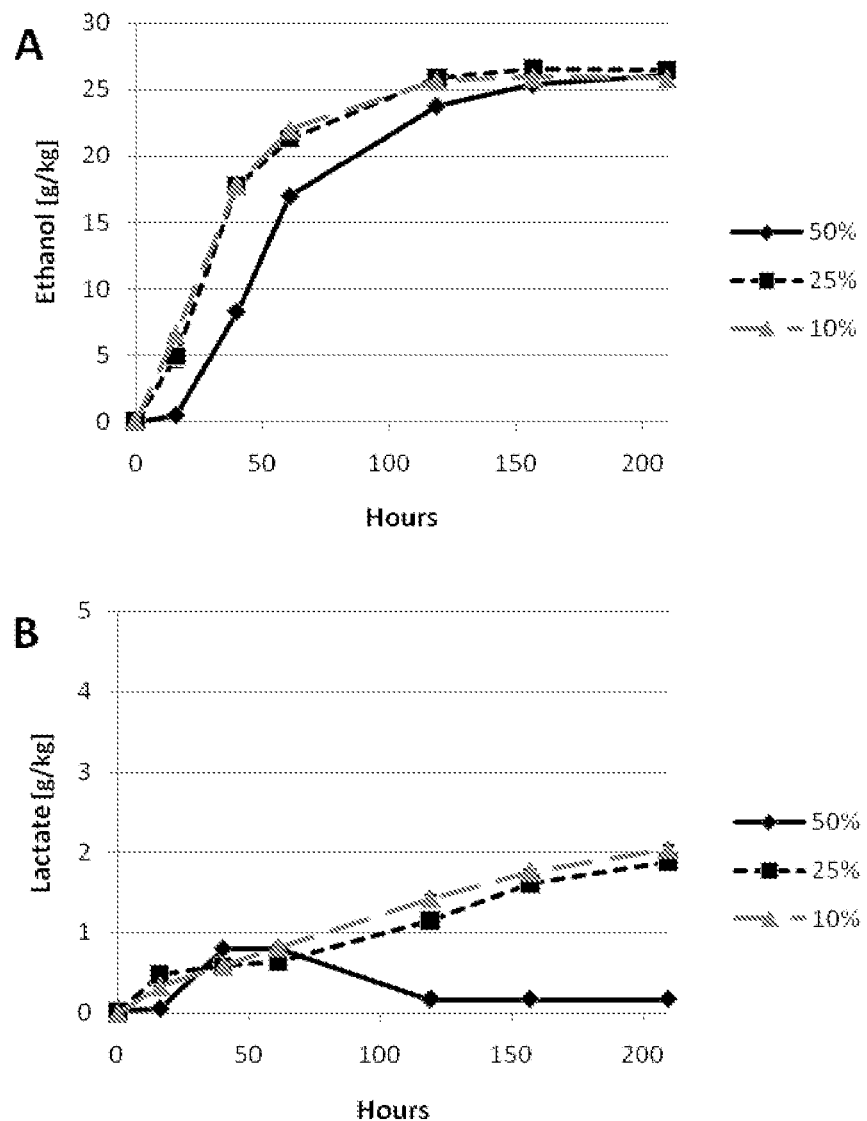
FIG. 10. Effects of varying concentrations of liquid fraction (%) on ethanol (A) and lactate (B) concentration during SSF of pretreated wheat straw.

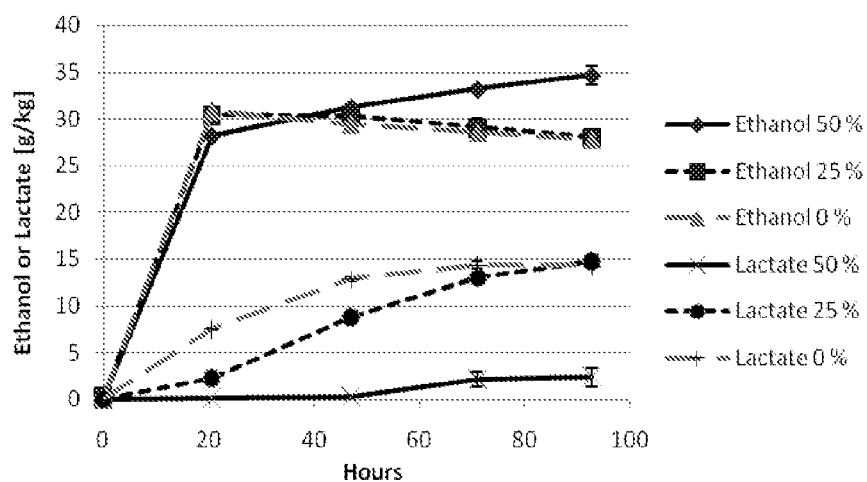
FIG. 11. Effects of varying concentrations of liquid fraction on ethanol and lactate concentrations in a first generation bioethanol process based on wheat flour.

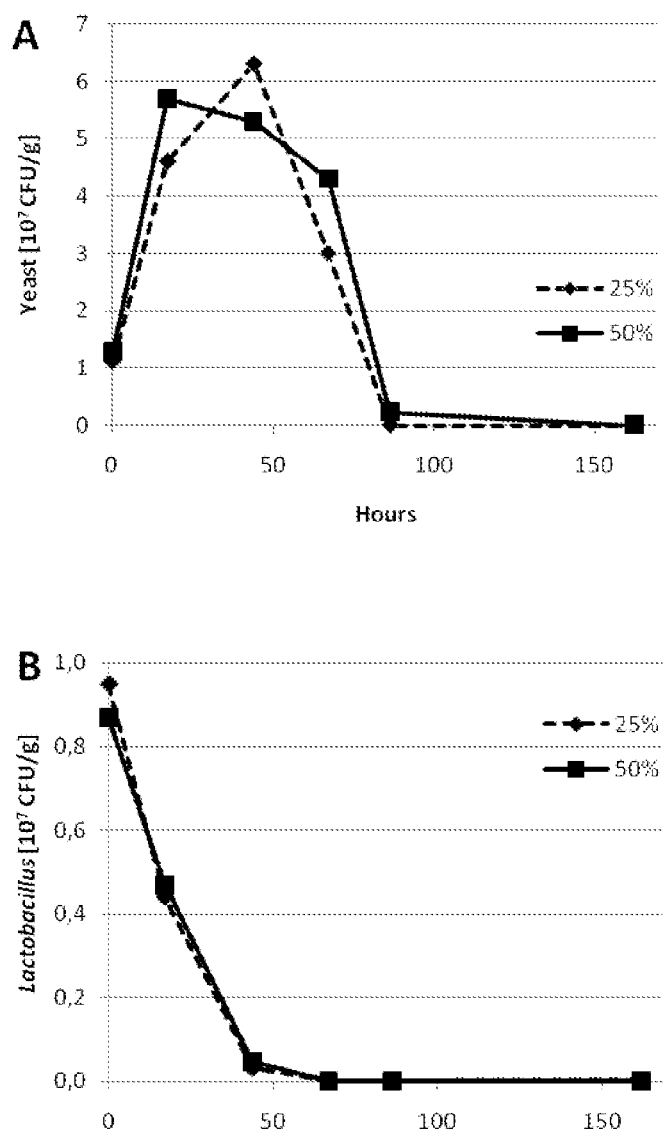
FIG. 12. Effects of inhibitor dilution on yeast CFU (A) and *Lactobacillus* CFU (B) during non-sterile fermentation of pretreated wheat straw.

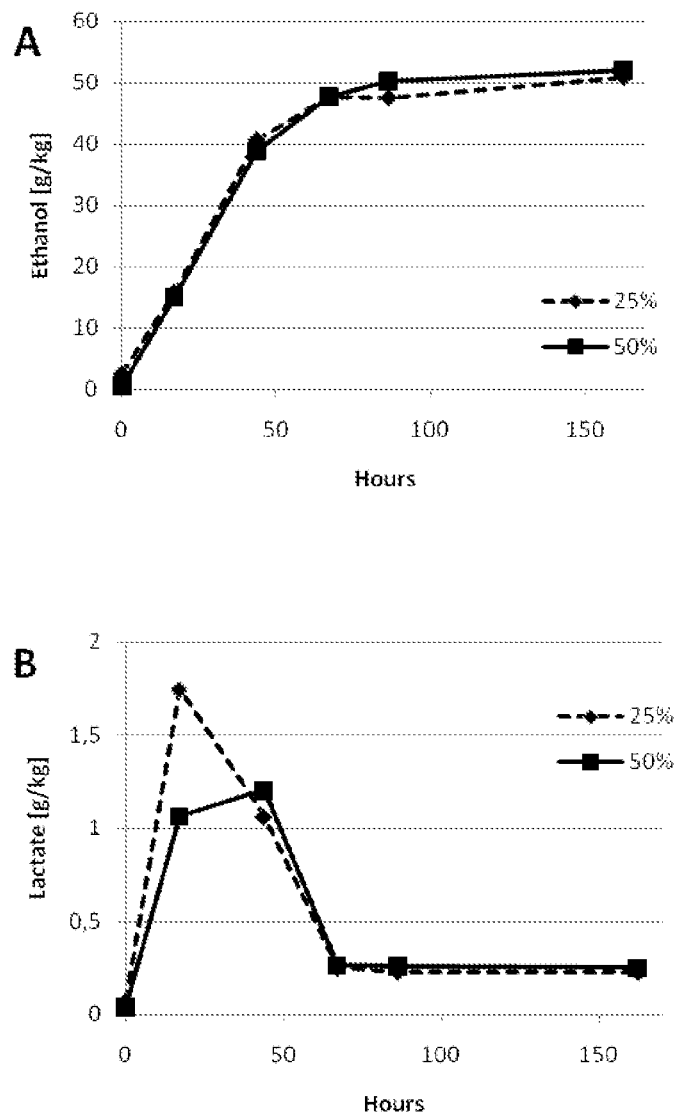
FIG. 13. Effects of inhibitor dilution on ethanol (A) and lactate (B) concentration during non-sterile fermentation of pretreated wheat straw.

US 8,703,453 B2

NON-STERILE FERMENTATION OF BIOETHANOL

This application is a divisional of application U.S. Ser. No. 12/808,746 filed Sep. 14, 2010, U.S. Pat. No. 8,187,849 which is a national stage entry of PCT/IB2008/003536, international filing date Dec. 18, 2008, which claims priority to U.S. 61/015,688, filed Dec. 21, 2007, and to PA 2007 01862, filed Dec. 21, 2007.

FIELD OF THE INVENTION

The invention relates in general to methods for fermentation of lignocellulosic and/or starch biomass and to methods for processing lignocellulosic feed stocks.

BACKGROUND

An intense interest has arisen in fermentation of carbohydrate-rich biomass to provide alternatives to petrochemical sources for fuels and for organic chemical precursors. "First generation" bioethanol production from starch sources such as corn or wheat have proved marginally economically viable on a production scale. "Second generation" bioethanol production from lignocellulosic feedstocks, including municipal and agricultural wastes, faces steeper obstacles to economic viability. Improvements that reduce costs or improve yields or efficiencies of either first or second generation bioethanol fermentation processes are, accordingly, advantageous.

One problem typically encountered in "second generation" bioethanol fermentation is the presence of degradation products arising from pretreatment of lignocellulosic feedstocks. These degradation products often act as fermentation inhibitors. The character and relative amounts of degradation products formed depend on the lignocellulosic feedstock used and on pretreatment conditions. For review, see ref. 1. In high temperature pretreatments, formation of degradation products is generally dependent on a combined severity factor, which relates reaction temperature and duration as well as pH. Sugar degradation products such as furfural and hydroxymethylfurfural (HMF) are formed in high temperature processes, in general, and in especially high concentrations during severe acid pretreatment. Acetic acid is ubiquitous in lignocellulose pretreatments, since hemicellulose and, to some extent, lignin are acetylated. Formic acid is, also, often formed as are a variety of monomeric phenolic compounds derived from lignin.

Four general strategies have previously been pursued for ameliorating deleterious impact of fermentation inhibitors. First, development of mild pretreatment conditions that minimize formation of inhibitory degradation products. Second, development of post-pretreatment processes that actively "detoxify" biomasses prior to fermentation. Third, selection and engineering of inhibitor-tolerant fermentive organisms. Finally, development of pretreatment processes that effectively detoxify inhibitors, such as "wet oxidation" in the presence of oxygen. For examples, see ref. 2, 3 and 4.

Another problem typically encountered in both "first" and "second generation" bioethanol fermentation is bacterial contamination of fermentation mixtures. In both first and second generation fermentation processes, bacterial contamination has proved difficult to avoid under non-sterile conditions. Lactic acid bacteria, in particular *Lactobacillus* species, are the primary bacterial contaminants of fuel ethanol fermentations. Production facilities routinely monitor lactic acid concentrations of fermentation mixtures as a measure of degree of contamination. Bacterial contamination reduces ethanol yields and, also, increases costs. Contamination has previously been controlled by addition of anti-bacterial agents or other asceptics or by pasteurization procedures between or during the course of fermentation runs. See e.g. ref. 5.

Here we report the surprising discovery that a range of concentrations exists in which fermentation inhibitors derived from pretreatments of lignocellulosic feed stocks will not affect fermentive yeast but will inhibit growth of lactic acid bacteria. By optimizing levels of fermentation inhibitors to fall within this range, yeast fermentations of lignocellulosic biomass can be conducted under non-sterile conditions with ethanol yields comparable to those achieved under sterile conditions. Fermentation inhibitors derived from pretreated lignocellulosic feed stocks can also be added to first generation starch fermentations, permitting normal ethanol yields under non-sterile conditions.

SUMMARY

Methods of bioethanol fermentation from starch and/or lignocellulosic biomass and methods of processing lignocellulosic biomass are provided. The concentration of fermentation inhibitors derived from pretreatment of lignocellulosic feed stock is controlled in a fermentation mixture to fall within ranges of concentrations that inhibit contaminating bacterial growth and/or lactate production while having substantially no effect on ethanol fermentive microorganisms. In preferred embodiments, this optimisation of inhibitor levels is achieved by controlling the water/biomass ratio of a lignocellulosic biomass during and after pretreatment. In some embodiments, the water/biomass ratio is controlled by washing the fiber fraction of a previously pretreated lignocellulosic biomass with a pre-defined amount of fresh water or recycled process solutions. Also provided are anti-bacterial compositions comprising fermentation inhibitors derived from pretreatment of lignocellulosic feedstocks.

BRIEF DESCRIPTION OF THE DRAWINGS

FIG. 1 shows a schematic illustration of process steps in pretreatment of lignocellulosic biomass.

FIG. 2 shows non-sterile pre-hydrolysis and fermentation of pretreated wheat straw having a water/biomass ratio of 5:1. Glucose, ethanol, lactate and glycerol concentrations are shown over the course of pre-hydrolysis and SSF.

FIG. 3 shows non-sterile pre-hydrolysis and fermentation of pretreated wheat straw having a water/biomass ratio of 5:1 (dotted curves) compared with 11:1 (full line curves). Lactate concentrations are shown over the course of pre-hydrolysis and SSF.

FIG. 4 shows non-sterile pre-hydrolysis and fermentation of pretreated bagasse having water/biomass ratio 5:1. Ethanol, glucose and lactate concentrations are shown over the course of the pre-hydrolysis and SSF.

FIG. 5 shows non-sterile pre-hydrolysis and fermentation of pretreated corn stover having water/biomass ratio 5:1. Ethanol, glucose and lactate concentrations are shown over the course of the pre-hydrolysis and SSF.

FIG. 6 shows effects of varying concentrations of liquid fraction from pretreated lignocellulosic biomass on yeast (A) and *Lactobacillus* (B) growth over the course of glucose fermentation.

FIG. 7 shows effects of varying concentrations of liquid fraction from pretreated lignocellulosic biomass on glucose fermentation by yeast and *Lactobacillus*. Ethanol (A) and lactate (B) concentrations are shown over the course of the process.

FIG. 8 shows effects of varying concentrations of liquid fraction from pretreated lignocellulosic biomass on glucose consumption by yeast and *Lactobacillus* during glucose fermentation.

FIG. 9 shows effects of varying concentrations of liquid fraction on yeast (A) and *Lactobacillus* (B) growth during SSF of pretreated wheat straw.

FIG. 10 shows effects of varying concentrations of liquid fraction on fermentation of pretreated wheat straw. Ethanol (A) and lactate (B) concentrations are shown over the course of the SSF process.

FIG. 11 shows effects of varying concentrations of liquid fraction on fermentation of hydrolysed wheat flour. Ethanol and lactate concentrations are shown over the course of the SSF process.

FIG. 12 shows effects of inhibitor dilution on yeast (A) and *Lactobacillus* (B) growth during non-sterile fermentation of pretreated wheat straw.

FIG. 13 shows non-sterile fermentation of pretreated wheat straw having water/biomass ratio 5:1 and further diluted with water or supplemented with liquid fraction. Ethanol (A) and lactate (B) concentrations are shown over the course of the SSF process.

DETAILED DESCRIPTION OF PREFERRED EMBODIMENTS

As used herein, the following terms have the following meanings:

(i). Starch Biomass

Starch biomass refers to material derived from plants or other organisms in which carbohydrate content includes at most a small component of cellulose and hemicellulose but includes a significant component of starch, amylose, amylopectin or similar substance. The term as used includes seeds, fruits, grains, roots, tubers, processed materials, such as waste foods, and starch rich components of fuel crops. Starch biomass will typically comprise water content. A mixture of water and/or other agents and/or solvents comprising starch biomass as the predominant solid component can also be referred to as "a" starch biomass within the meaning of the term as used.

(ii). Lignocellulosic Biomass

Lignocellulosic biomass refers to material derived from plants or other organisms in which carbohydrate content includes a substantial component of cellulose and hemicellulose and which comprises more than 5% lignin. The term as used includes material that is predominantly cellulose and hemicellulose as well as material that includes starch content, including agricultural wastes, whole crops, substantially whole crops, stems, stalks, leaves, starch-rich components, and processed materials, such as papers. A lignocellulosic biomass may comprise a starch biomass. Lignocellulosic biomass will typically comprise water content. A mixture of water and/or other agents and/or solvents comprising lignocellulosic biomass as the predominant solid component can also be referred to as "a" lignocellulosic biomass within the meaning of the term as used. The carbohydrate composition of a lignocellulosic biomass may be changed during pretreatment.

(iii). Initially Pretreated, Pretreatment and Post Pretreatment Processing

Pretreatment refers to a manipulation of lignocellulosic biomass that renders its cellulosic component more accessible to enzymes that convert carbohydrate polymers into fermentable sugars. "Initially pretreated" refers to a lignocellulosic biomass that has been subjected to at least one pretreatment. A lignocellulosic biomass may be pretreated and then, subsequently, subject to post pretreatment processing that enhances yield or efficiency of fermentation or otherwise facilitates production scale operations. The fiber fraction of a pretreated lignocellulosic biomass may comprise all or part of dry matter obtained from pretreated biomass.

(iv). Fermentation Inhibitor

Fermentation inhibitor refers to lignocellulose degradation products that can inhibit growth of fermentive microorganisms at concentrations that can be achieved in common lignocellulosic feedstock mixtures after thermal or acid pretreatment. Fermentation inhibitors as used herein may include any of furfural, 5-hydroxymethylfurfural, acetic acid, phenol, catechol, coniferyl alcohol, furfuryl alcohol, guaiacol, hydroquinone, methylcatechol, vanillyl alcohol, eugenol, isoeugenol, syringol, 4-hydroxybenzaldehyde, 4-hydroxybenzalcohol, 4-hydroxybenzoic acid, 3-hydroxybenzoic acid, 2-hydroxybenzoic acid, 2,5-dihydroxybenzoic acid, 2,6-dimethoxy-hydroquinone, 2-methylphenol, ethylcatechol, d-furoic acid, syringic acid, 4-hydroxycinnamic acid, ferulic acid, vanillin, iso-vannillin, ortho-vanillin, syringaldehyde, vanillic acid, acetovanillone, acetosyringone, dihydroconiferyl acicohol, coniferly aldehyde, p-coumaric acid, formic acid, levulinic acid, caproic acid, 2-furoic acid, gallic acid, protocatechuic acid, homovanillic acid, 4-hydroxy acetophenone, trimethothy benzaldehyde, trimethoxyacetophenone, or other lignocellulosic degradation products not currently known that may subsequently be identified. The term "fermentation inhibitor" as used here is distinct from "anti-bacterial agents" and "asceptics," which are not derived from lignocellulose degradation.

(v). Severity Index

Severity index refers to an optimization parameter for pretreatment relating the combined effect of treatment time and temperature which is typically written as:

$$Ro = t_r \exp[(T_r - 100)/14.75]$$

where $t_r$ is reaction time in minutes and $T_r$ is reaction temperature.

(vi). Amount of Fermentation Inhibitors Initially Present

The expression "amount of fermentation inhibitors initially present" in a pretreated lignocellulosic biomass refers to the amount present after an initial pretreatment to combined severity index at least 3.0 but before any subsequent pretreatments, washing steps or post pretreatment processing.

(vii). Sterile Conditions

Sterile conditions refers to fermentation conditions in which effective amounts of asceptics or anti-bacterial agents other than fermentation inhibitors, as defined herein, have been added, or in which procedures have been employed to sterilize the fermentation vessel. Effective amounts of asceptics or anti-bacterial agents are amounts that would be sufficient, in the absence of fermentation inhibitors, to suppress bacterial growth and/or lactate production such that lactate yield in the fermentation mixture after the desired part of fermentable sugars have been converted would be lower than about 4 g/kg.

(viii). Non-Sterile Conditions

Refers to fermentation conditions other than "sterile conditions" as defined herein.

(ix). Fermentation Mixture

Refers to a mixture comprising starch and/or pretreated lignocellulosic biomass and one or more ethanol fermentive microorganisms. A fermentation mixture may comprise the fiber fraction of a pretreated lignocellulosic biomass that has been previously subject to partial or complete enzymatic hydrolysis and/or used in a simultaneous saccharification and fermentation process. A fermentation mixture may comprise a starch biomass, a lignocellulosic biomass or a mixture of both. A fermentation mixture may be a continuous or semi-continuous culture, batch or fed-batch fermentation mixture.

(x) Ethanol Yield

Ethanol yield refers to the amount of ethanol produced from a certain amount of fermentable sugars. An example is: In a fermentation mixture comprising 30 g/kg of glucose, the fermentive microorganism converts all the glucose and the result is a fermentation mixture comprising 15 g/kg of ethanol. The ethanol yield is 0.50 g ethanol/g glucose. Another example is a fermentation mixture comprising 45 g/kg cellulose, from which 30 g/kg glucose are released. The % conversion of cellulose is 67%. The ethanol yield is 0.50 g ethanol/g glucose. The term "theoretical yield" refers to yeast efficiency in fermentation of glucose. In both examples, theoretical yield is 98%.

(xi). Optimised Levels of Fermentation Inhibitors

The expression "optimised levels" of fermentation inhibitors refers to levels of fermentation inhibitors achieved by controlling the water/biomass ratio of a pretreated biomass or by otherwise adjusting the amounts present in a pretreated lignocellulosic biomass and/or in a fermentation mixture in such manner that when the pretreated lignocellulosic biomass is fermented in a fermentation mixture or when the fermentation mixture containing optimised levels is fermented, contaminating bacterial growth and/or lactate production is substantially inhibited while ethanol fermentative yeast are substantially unaffected. Bacterial growth and/or lactate production is substantially inhibited where the lactate yield in the fermentation mixture after the desired part of fermentable sugars have been converted is lower than about 4 g/kg. Ethanol fermentative yeast are substantially unaffected where the yeast strains produce ethanol yields higher than about 75% theoretical yield. Adjustment to optimized levels of fermentation inhibitors may include increasing levels by addition of fermentation inhibitors derived from a pretreated lignocellulosic biomass, or decreasing levels.

(xii) Fiber Fraction of a Pretreated Lignocellulosic Biomass

Fiber fraction of a pretreated lignocellulosic biomass is obtained from pretreatment and/or post-pretreatment processes in which pretreated biomass is separated into at least two fractions, one comprising predominantly liquid, and one comprising predominantly insoluble materials. The fiber fraction is that fraction comprising predominantly insoluble materials. The liquid fraction and fiber fraction may be separated in multiple steps. For example, a pretreated biomass may be pressed once, separating a liquid and fiber fraction, then subsequently washed and pressed again, separating, again, a liquid and fiber fraction. A fiber fraction may be subject to enzymatic or chemical hydrolysis and liquefaction prior to use in a fermentation mixture.

(xiii). Water/Biomass Ratio

Water/biomass ratio refers to the ratio between the initial non-water content of a lignocellulosic biomass prior to pretreatment and the total amount of water to which this material is exposed during and after pretreatment, including water present in the biomass as it is pretreated and water introduced during pretreatment and post pretreatment processing, except for water that is added separately in dilution of liquid fraction. Water may be added as fresh water, condensate, recycled process solutions or any combination thereof. Processing may include wash steps, preparation of fermentation mixtures, introduction to continuous fermentation mixtures, and other processes after pretreatment but preceding final ethanol yields. An example calculation of water/biomass ratio is the following: 50 kg wheat straw having non-water content 92.0% is subject to pretreatment involving soaking in dilute acid, steam treatment, washing after steam treatment and pressing to a pretreated fiber fraction weighing 100 kg and having water content 64.8%. The total mass of wash effluent and solution pressed from the biomass is 180 kg having water content 94.0% and dissolved solutes 6%. The fiber fraction is directly subject to pre-hydrolysis and simultaneous saccharification and fermentation, without further addition of water. The water/biomass ratio is, thus, 5:1−[169.2 kg water ((180 kg×94.0% water)+64.8 kg water (100 kg×64.8% water))=234 kg water]/[46 kg initial non-water content (50 kg×92.0%)].

We have discovered that, surprisingly, levels of fermentation inhibitors derived from lignocellulose degradation can be optimised in bioethanol fermentation mixtures such that ethanol fermentive microorganisms are substantially unaffected while contaminating lactic acid bacteria are effectively inhibited.

Accordingly, in some embodiments, the invention provides a method of processing lignocellulosic biomass comprising preparing a non-sterile fermentation mixture comprising the fiber fraction of a pretreated lignocellulosic biomass and optimised levels of fermentation inhibitors that inhibit contaminating bacterial growth and/or lactate production while having substantially no effect on ethanol fermentive yeast.

In other embodiments, the invention provides a method of fermentation of lignocellulosic biomass comprising the steps of preparing a non-sterile fermentation mixture comprising the fiber fraction of a pretreated lignocellulosic biomass and optimised levels of fermentation inhibitors that inhibit contaminating bacterial growth and/or lactate production while having substantially no effect on ethanol fermentive yeast;

fermenting said fermentation mixture.

In still other embodiments, fermentation inhibitors derived from pretreatment of lignocellulosic biomass can be added to optimised levels in fermentation mixtures comprising primarily starch biomass. This provides a cost-saving alternative to traditional methods of contamination control in bioethanol production.

In still other embodiments, the invention provides antibacterial compositions comprising a crude extract of liquid fraction from pretreatment of lignocellulosic biomass.

FIG. 1 provides a schematic illustration of process steps in pretreatment of lignocellulosic biomass. As shown, in some pretreatment methods, lignocellulosic biomass is pretreated in such manner as provides a slurry, having no separation of liquid and fiber fraction. Lignocellulosic biomass pretreated by these methods is not suited for practice of embodiments of the invention. Other pretreatment methods, as shown, provide a separation of pretreated lignocellulosic biomass into at least two fractions, a liquid fraction and a fiber fraction. In these pretreatment methods, lignocellulosic biomass can be washed, soaked or wetted outside a pressurized reactor prior to pretreatment. After pretreatment, water can be added in further soaking or washing steps, followed by one or more pressing steps which separates a liquid fraction from a fiber fraction. The "fiber" fraction comprises dry matter as well as some water and solute content. The liquid fraction may contain a high percentage of dissolved sugars in addition to fermentation inhibitors. Lignocellulosic biomass pretreated and processed so as to provide a fiber fraction is suited for practice of embodiments of the invention.

In some pretreatment processes, water content may be introduced during pretreatment by co-current, counter-current, or flow-through methods described in ref. 6.

In preferred embodiments, the fiber fraction of a lignocellulosic biomass is suitable for use on a large scale, having dry matter mass at least 40 kg, or greater than 100 kg, or greater than 1000 kg, or greater than 10,000 kg.

In the practice of some embodiments of the invention, any suitable lignocellulosic biomass feedstock may be used including at least corn stover, wheat straw, rice straw, bagasse, corn fiber, agricultural wastes, plant stalks, hardwood bulk, softwood bulk, nut shells, empty fruit bunches, corn cobs, grasses, including coastal Bermuda grass and switch grass, paper, including newspaper, waste papers and paper from chemical pulps, sorted refuse, cotton seed hairs, and other materials well known in the art.

Lignocellulosic biomass feedstocks may be pretreated and processed by simple methods that avoid excessive degradation of feedstocks and that provide separation of pretreated biomass into at least a liquid and a fiber fraction. Suitable pretreatment methods include at least steam explosion, high pressure steam, liquid hot water, and dilute acid. Many variants of these pretreatment processes are suitable and well known in the art. In preferred embodiments, feedstocks are pretreated to severity at least 3.0.

Different fermentation inhibitors are produced in different amounts, depending on the properties of the lignocellulosic feedstock and on the method of pretreatment used. See ref. 1. At least three categories of fermentation inhibitors are typically formed during pretreatment: (1) furans, primarily 2-furfural and 5-HMF (5 hydroxymethylfurfural) which are degradation products from monosaccharides; (2) monomeric phenols, which are degradation products of the lignin structure; and (3) small organic acids, primarily acetic acid, which originate from acetyl groups in hemicelluloses and lignin.

The mixture of different inhibitors has been shown to act synergistically in bioethanol fermentation using yeast strains (ref. 7) and, also, using ethanolic *Escherichia coli* (ref. 8). During the course of fermentation, some inhibitors are consumed, the concentrations of others remain constant, while still others are actively accumulated, including acetic acid.

A suitable source for fermentation inhibitors that can provide optimised levels is any lignocellulosic feedstock that gives rise to the following inhibitors when pretreated with heat and/or acid conditions: Furfural, hydroxymethylfurfural, acetic acid, and monomeric phenols including any of syringaldehyde, vanillin, homovanillic acid, syringic acid, p-coumaric acid, and ferulic acid. Preferred feedstocks when pretreated by heat and/or acid conditions may also give rise to additional inhibitors, but at typically lower levels, including acetosyringone, 4-OH benzaldehyde, phenol, guaiacol, syringol, 4-OH benzylalcohol, trimethoxybenzaldehyde, trimethoxyacetophenone, 4-OH acetophenone, acetovanillone, vanillyl alcohol, 4 OH benzoic acid and vanillic acid. Preferred feedstocks may also give rise to formic and levulinic acid.

The concentration of fermentation inhibitors generated during pretreatment which is required to achieve optimised levels will vary depending on severity of pretreatment and choice of lignocellulosic feedstock. However, an appropriate dilution suitable to achieve optimised levels can be readily determined through routine experimentation.

Biochemical mechanisms are not currently known whereby fermentation inhibitors exhibit a differential effect on lactic acid bacteria compared with ethanol fermentative yeast. Many fermentation inhibitors commonly generated during pretreatment of lignocellulosic biomass were previously reported to exhibit some anti-bacterial effect, although at higher concentrations than those typically achieved in wash water from pretreated biomass. For examples involving p-coumaric acid, vanillic acid, p-hydroxybenzoic acid, syringic acid, and ferulic acid see refs. 9, 10, 11, 12 and 13. Possibly, some previously unknown synergisms provide a cumulative anti-bacterial effect, at much lower concentrations, involving a "cocktail" of inhibitors.

In some embodiments, such a "cocktail" of inhibitors generated during pretreatment of lignocellulosic biomass may be up-concentrated and provided for use in contamination control of starch or first generation bioethanol fermentation.

In preferred embodiments, a fermentation mixture comprising optimised levels of fermentation inhibitors is prepared by controlling the water/biomass ratio, in particular, by washing the fiber fraction of a pretreated lignocellulosic feedstock with a pre-defined quantity of water or process solutions that provides a definite water/biomass ratio. For example, with wheat straw, and other lignocellulosic feedstocks having compositions of hemicellulose, cellulose and lignin similar to wheat straw, including bagasse, and corn stover pretreated to combined severity index 3.5-4.0, optimised levels of fermentation inhibitors can typically be achieved by washing the pretreated biomass with fresh water or recycled process waters to achieve a water/biomass ratio of between 1:4 and 1:8. It will be readily understood by one skilled in the art that aqueous solutions derived from liquid fraction, washing/pressing steps, or other processes can be used in water recycling schemes. In such cases, fermentation inhibitors may accumulate such that an overall appropriate water/biomass ratio may be higher.

Using routine experimentation, one skilled in the art will readily arrive at an appropriate water/biomass ratio for a given lignocellulosic feedstock subject to a given pretreatment. It will be readily understood that, where a given lignocellulosic biomass is pretreated to higher severity index, a higher water/biomass ratio may be required to achieve optimised levels of fermentation inhibitors. Similarly, where a given lignocellulosic biomass is pretreated to lower severity index, a lower water/biomass ratio may be required to achieve optimised levels of fermentation inhibitors. For example, the fiber fraction of a pretreated lignocellulosic feedstock is first tested directly in a non-sterile fermentation mixture without any wash or effort to reduce or ameliorate fermentation inhibitors. If both lactate and ethanol production appear to be relatively un-inhibited, fermentation inhibitors can be added to optimised levels. In other circumstances, washing steps can be conducted in increments of water/biomass ratio until an appropriate range of wash conditions is identified that will provide optimised levels of fermentation inhibitors in a fermentation mixture. In circumstances where fermentation inhibitors must be added to achieve optimised levels of fermentation inhibitors, one skilled in the art will readily determine, with routine experimentation, an appropriate amount to add of wash water, liquid fraction or up-concentrated inhibitors from a given lignocellulosic feedstock subject to a given pretreatment.

To achieve optimised levels of fermentation inhibitors in a fermentation mixture comprising primarily starch biomass, liquid fraction or up-concentrated inhibitors can be added that were derived from liquid fraction or wash waters from post-pretreatment processing of lignocellulosic biomass. With routine experimentation, one skilled in the art will readily arrive at an appropriate amount of inhibitors to add to a fermentation mixture comprising primarily starch biomass so as to achieve optimised levels of fermentation inhibitors.

Washing of pretreated lignocellulosic feedstocks can be achieved by a number of different methods. In preferred embodiments, as shown in FIG. 1, pretreated lignocellulosic biomass is further subject to any number of washing/soaking and pressing steps. In other embodiments, water content may be introduced during pretreatment to such levels that optimised levels of fermentation inhibitors can be achieved using only pressing steps or other methods for separating the fiber fraction. In still other embodiments, an appropriate water/biomass ratio may be achieved that will provide optimised levels of fermentation inhibitors by introducing water content prior to pretreatment and subsequently separating a fiber fraction by pressing or other methods.

A fermentation mixture comprising a fiber fraction of a lignocellulosic biomass can be prepared by a variety of different methods. In some embodiments, the fiber fraction comprising dry matter and water content can be used in simultaneous saccharification and fermentation by introducing fermentive microorganisms and hydrolytic enzymes essentially simultaneously. In some embodiments, the fiber fraction comprising dry matter and water content may be supplemented with additional water content and/or wash water from a pretreated lignocellulosic biomass and/or other chemicals or additives including, for example, surfactants and lignin-binding agents. In some embodiments, saccharification and liquefaction of the fiber fraction may be acheived in one step, with fermentive organisms added subsequently to provide a fermentation mixture. In some embodiments, the fiber fraction with or without additives may be subject to an initial pre-hydrolysis using hydrolytic enzymes, with subsequent simultaneous saccharification and fermentation. In some embodiments, fermentation may be conducted in an essentially batch manner. In some embodiments, a continuous or semi-continuous stream of fiber fraction of pretreated lignocellulosic biomass may be introduced to a pre-hydrolysis reactor to which hydrolytic enzymes are similary introduced in a continuous or semi-continuous stream. In these embodiments, the water/biomass ratio may be adjusted to levels that achieve optimised levels of fermentation inhibitors before the fiber fraction enters pre-hydrolysis. Levels of fermentation inhibitors may also be optimised by subsequent additions in pre-hydrolysis prior to introduction of ethanol fermentive microorganisms or in fermentation mixtures. In some embodiments, fermentation may be conducted in a continuous culture, to which pretreated and pre-hydrolysed lignocellulosic biomass can be introduced. Other embodiments of the invention can also be imagined by one skilled in the art. Fermentation inhibitors can also be isolated and/or concentrated to provide anti-bacterial compositions. Crude extracts of liquid fraction or wash waters provide effective and inexpensive anti-bacterial activity suitable for use in a variety of industrial or other settings. Crude extracts of liquid fraction may be prepared by a variety of methods known in the art and may be partially purified, in that particularly useful components such as C5 sugars may be removed, or particularly hazardous or unwanted materials removed. In preferred embodiments, a portion of liquid fraction remaining after useful C5 sugars have been removed may simply be concentrated to a concentrated liquid. Because many important inhibitors are volatile, precautions are advisable to avoid evaporative losses. Accordingly, ultrafiltration techniques are generally preferable for concentration of inhibitor solutes. The crude extract of liquid fraction can be further partially purified. The concentrated, optionally partially purified, crude extract can be used as a cheap alternative to hops or other anti-bacterial or asceptic agents in first generation bioethanol fermentations of primarily starch biomass. The material may further be used as an anti-bacterial composition in other, non-ethanol yeast fermentations, in fermentations involving other inhibitor-tolerant microorganisms, and in "training" inhibitor tolerance of fermentive microorganisms, for example, as described in ref. 14 and 15.

Preferred ethanol fermentive yeast that can be used to practice embodiments of the invention include wild type strains of *Saccharomyces cerevisiae* and other strains which have been adapted for use in ethanol fermentation. For example, each of the following yeast strains obtained from Ethanol Technology were effective: (a). THERMOSACC™: This is a stress tolerant yeast, with good tolerance to high temperatures, high organic acids and high osmotic pressure that occur in high-gravity fermentations. This yeast works well at temperatures up to 37° C. and alcohol concentrations of more than 20% by volume (16% by weight). Glycerol production is lower. This yeast can take short exposure to 40° C. and still complete the fermentation. (b). SUPERSTART™: This is an older distilling yeast strain. This yeast is good for fermenting maltose and maltotriose. This yeast has been used in high gravity fermentations reaching 23% alcohol by volume on a wheat substrate. SUPERSTART™ is long-lived and resilient in continuous fermentation conditions. (c). CAT 1™: This is a very robust yeast most often used in continuous or recycling operations. It is resistant to mutations and is able to dominate fermentations. It has good resistance to low pH.

Suitable "untrained" ethanol fermentive yeast include any strains that have tolerance comparable or greater than wild type *Saccharomyces cerevisiae* to a mixture of 5 hydroxymethyl furfural, furfural, acetic acid, vanillin, syringaldehyde, vanillic acid, homovanillic acid, syringic acid, p-coumaric acid, and ferulic acid.

Optimised levels of fermentation inhibitors are effective against a variety of lactic acid bacteria, including but not limited to species of the genera *Lactobacillus, Leuconostoc, Pediococcus, Lactococcus, Streptococcus, Aerococcus, Carnobacterium, Enterococcus, Oenococcus, Teragenococcus, Vagococcus*, and *Weisella*.

EXAMPLE 1

Achieving Optimised Levels of Fermentation Inhibitors for Non-Sterile Fermentation of Steam Pretreated Wheat Straw by Controlling the Water/Biomass Ratio in the Pretreatment and Post-Pretreatment Processing Experiments were conducted at the Inbicon pilot plant in Fredericia, Denmark. Cut wheat straw (average particle size of approximately 40 mm), 50 kg/hour having 92.0% initial non-water content, was continuously pretreated by steam at 185-200° C. for 10-15 minutes. The pretreatment must be sufficient to ensure that the structure of the lignocellulosic content is rendered accessible to hydrolytic enzymes. In order to achieve appropriate levels of fermentation inhibitors, the pretreated wheat straw was subject to post-pretreatment processing consisting of a washing and pressing step. The pretreated wheat straw was washed by water in such manner as to achieve a water/biomass ratio of 5:1, in one experiment, and 11:1 in an otherwise identical experiment.

After washing and pressing, the liquid fraction comprised fermentation inhibitors, hemicellulose and other soluble components. The fiber fraction comprised insoluble fibers and had a dry matter content of approximately 26%. The fiber fraction was pre-hydrolysed by means of addition of NOVOZYM 188™ and CELLUCLAST 1.5 FG™ (Novozymes, A/S) at 50° C. The pre-hydrolysed fiber fraction was subsequently used to prepare a fermentation mixture by adding common bakers yeast (Baker's yeast, *Saccharomyces cerevisiae* obtained from De Danske Spritfabrikker) without further addition of water or other agents. The fermentation mixture was simultaneously saccharified and fermented (SSF) at 30-33° C. The SSF was conducted in a non-sterile free fall mixer according to the process described by WO2006/056838, which is hereby incorporated by reference in entirety. The fermentation mixture was not sterilised before the experiment and was opened daily during the fermentation time of up to 400 hours to take out samples.

Results are presented in FIGS. 2 and 3. FIG. 2 shows glucose, ethanol, lactate and glycerol concentrations over the course of pre-hydrolysis and SSF of pretreated wheat straw having water/biomass ratio 5:1. As shown, less than 2 g/kg of glucose was detected after 30 hours. This indicates that the yeast was capable of utilising all glucose produced during pre-hydrolysis and later all glucose produced during SSF as the ethanol concentration in the fermentation mixture was still increasing after 170 hours of fermentation. Less than 1 g/kg of lactate was detected after 170 hours of fermentation showing that lactate-producing bacterial growth and/or lactate production were substantially inhibited in the non-sterile fermentation conditions.

FIG. 3 shows lactate concentrations over the course of fermentation in fermentation mixtures prepared from the fiber fraction of pretreated and washed wheat straw having water/biomass ratio 11:1 or 5:1. As shown, in fermentation mixtures prepared from the fiber fraction having water/biomass ratio 11:1, lactate concentrations increased from below 1 g/kg after 48 hours to approximately 8 g/kg after 150 hours. In contrast, in fermentation mixtures prepared from the fiber fraction having water/biomass ratio 5:1, lactate concentrations remained beneath 1 g/kg throughout the course of the fermentation process.

EXAMPLE 2

Non-Sterile Fermentation of Steam Pretreated Bagasse Using Levels of Fermentation Inhibitors Optimised by Controlling the Water/Biomass Ratio Experiments were conducted at the Inbicon pilot plant in Fredericia, Denmark. Cut bagasse from US (average particle size of approximately 40 mm), 50 kg/h having 92.0% initial non-water content, was continuously pretreated by steam at 185-200° C. for 10-15 minutes. Conditions were not optimized for maximum ethanol yield. In order to achieve appropriate levels of fermentation inhibitors, the pretreated bagasse was subject to post-pretreatment processing consisting of a washing and pressing step. The pretreated bagasse was washed by water in such manner as to achieve a water/biomass ratio of 5:1.

After washing and pressing, the liquid fraction comprised fermentation inhibitors, hemicellulose and other soluble components. The fiber fraction comprised insoluble fibres and had a dry matter content of approximately 26%. The fiber fraction was pre-hydrolysed by means of addition of NOVOZYM 188™ and CELLUCLAST 1.5 FG™ at 50° C. The pre-hydrolysed fiber fraction was subsequently used to prepare a fermentation mixture by adding THERMOSACC™ (obtained from Ethanol Technology) without further addition of water or other agents. The fermentation mixture was simultaneously saccharified and fermented (SSF) at 30-33° C. The SSF was conducted in a non-sterile free fall mixer, according to the process described by WO2006/056838. The fermentation mixture was not sterilised before the experiment and was opened daily during the fermentation time of up to 200 hours to take out samples.

Results are presented in FIG. 4, which shows ethanol, glucose and lactate concentration over the course of the SSF process. As shown, less than 2 g/kg of glucose was detected after 30 hours. This indicates that the yeast was capable of utilising all glucose produced during pre-hydrolysis and, later, all glucose produced during SSF, as the ethanol concentration in the fermentation mixture was still increasing after 150 hours of fermentation. Less than 1 g/kg of lactate was detected after 170 hours of fermentation showing that lactate-producing bacterial growth and/or lactate production were substantially inhibited in the non-sterile fermentation conditions.

EXAMPLE 3

Non-Sterile Fermentation of Steam Pretreated Corn Stover Using Levels of Fermentation Inhibitors Optimised by Controlling the Water/Biomass Ratio Experiments were conducted at the Inbicon pilot plant in Fredericia, Denmark. Cut corn stover from Hungary (average particle size of approximately 40 mm), 50 kg/h having 92.0% initial non-water content, was continuously pretreated by steam at 185-200° C. for 10-15 minutes. Conditions were not optimized for maximum ethanol yield. In order to achieve appropriate levels of fermentation inhibitors, the pretreated corn stover was subject to post-pretreatment processing consisting of a washing and pressing step. The pretreated corn stover was washed by water in such manner as to achieve a water/biomass ratio of 5:1.

After washing and pressing, the liquid fraction comprised fermentation inhibitors, hemicellulose and other soluble components. The fiber fraction comprised insoluble fibres and had a dry matter content of approximately 26%. The fiber fraction was pre-hydrolysed by means of addition of NOVOZYM 188™ and CELLUCLAST 1.5 FG™ (Novozymes A/S) at 50° C. The pre-hydrolysed fiber fraction was subsequently used to prepare a fermentation mixture by adding THERMOSACC™ (obtained from Ethanol Technology) without further addition of water or other agents. The fermentation mixture was simultaneously saccharified and fermented (SSF) at 30-33° C. The SSF was conducted in a non-sterile free fall mixer according to the process described by WO2006/056838. The fermentation mixture was not sterilised before the experiment and was opened daily during the fermentation time of up to 200 hours to take out samples.

Results are presented in FIG. 5, which shows ethanol, glucose and lactate concentrations over the course of the SSF process. As shown, less than 3 g/kg of glucose was detected after 43 hours. This indicates that the yeast was capable of utilising all glucose produced during pre-hydrolysis and later all glucose produced during SSF. Less than 1 g/kg of lactate was detected after 163 hours of fermentation showing that lactate-producing bacterial growth and/or lactate production were substantially inhibited in the non-sterile fermentation conditions.

EXAMPLE 4

Concentration of Selected Fermentation Inhibitors During Hydrolysis and Fermentation of Pretreated Wheat Straw Having a Water/Biomass Ratio of 5:1

Levels of selected fermentation inhibitors during hydrolysis and fermentation achieved in the experiments described in Example 1 were measured by HPLC and are shown in Table 1. Individual measurements are means of duplicate experiments. Values are expressed as parts per million for all inhibitors except furfural and 5 hydroxymethylfurfural, which are expressed in g/l. Parts per million as used here refers to g/1,000,000 g. The mash used for inhibitor measurements during fermentation contained approximately 26% dry matter (insoluble material) and had a density of about 1.2 kg/L.

TABLE 1

Levels of inhibitors during hydrolysis (first 6 hours, at 50° C.)
and fermentation at 33° C. (yeast added after 6 hours), at 26% dry matter.

| | Hours | | | | | | | | | | |
|---|---|---|---|---|---|---|---|---|---|---|---|
| | 0 | 5.75 | 18.75 | 40 | 65.5 | 93.5 | 117.5 | 135.5 | 158.25 | 180.75 | 207.5 |
| 5 HMF | 0.100 | 0.124 | 0 | 0 | 0 | 0 | 0 | 0 | 0 | 0 | 0 |
| Furfural | 0.133 | 0.141 | 0 | 0 | 0 | 0 | 0 | 0 | 0 | 0.013 | 0.024 |
| 2-furoic acid | 24 | 30 | 28.5 | 24.5 | 23 | 24 | 24 | 23 | 21.5 | 24 | 21.5 |
| Phenol | 1 | 1.5 | 2 | 1 | 1 | 1 | 1.5 | 2 | 2 | 1.5 | 1 |
| Gualacol | 1 | 1 | 4.5 | 8.5 | 10.5 | 13 | 13 | 14 | 13 | 14.5 | 15 |
| Syringol | 4.5 | 4.5 | 3.5 | 3.5 | 3.5 | 3.5 | 4.5 | 4.5 | 4.5 | 4 | 3.5 |
| 4-OH benzaldehyd | 0 | 5 | 0 | 0 | 0 | 0 | 0 | 0 | 0 | 0 | 0 |
| Vanillin | 6.5 | 6.5 | 0 | 0 | 0 | 0 | 0 | 0 | 0 | 0 | 0 |
| Syringaldehyd | 5 | 5.5 | 14 | 9.5 | 6.5 | 5 | 3.5 | 3 | 3 | 3.5 | 2.5 |
| 4-OH benzylalcohol | 0.5 | 0.5 | 2 | 2.5 | 2 | 2 | 2 | 2 | 2 | 2 | 2 |
| Trimethoxybenzaldehyd | 0 | 1 | 0 | 0 | 0 | 0 | 0 | 0 | 0 | 0 | 0 |
| Trimethoxyacetophenon | 0 | 0 | 0 | 0 | 0 | 0 | 0 | 0 | 0 | 0 | 0 |
| 4-OH acetophenone | 3.5 | 3.5 | 2.5 | 2 | 2 | 3 | 3.5 | 3 | 3 | 2.5 | 2 |
| Acetovanillone | 0 | 1 | 8 | 0 | 0 | 0 | 0 | 0 | 0 | 0 | 0 |
| Acetosyringone | 3.5 | 3.5 | 2.5 | 1 | 1 | 1 | 2.5 | 2 | 2 | 1.5 | 2 |
| Vanillyl alcohol | 0 | 0 | 13.5 | 13 | 13 | 12 | 12 | 10.5 | 10.5 | 13 | 10 |
| 4-OH benzoic acid | 2 | 0 | 1 | 2 | 2 | 2 | 2 | 2 | 2 | 2 | 2 |
| Vanillic acid | 4.5 | 5 | 5.5 | 5 | 5 | 6 | 5 | 5.5 | 5.5 | 5.5 | 5.5 |
| Homovanillic acid | 3 | 4 | 19 | 21 | 21.5 | 22.5 | 22.5 | 22.5 | 21 | 21 | 20.5 |
| Syringic acid | 7 | 6 | 5 | 4 | 4 | 4.5 | 5 | 4.5 | 4 | 5 | 4.5 |
| Coumaric acid | 9.5 | 7 | 6.5 | 6 | 5 | 5 | 5 | 5 | 4 | 3.5 | 4 |
| Ferulic acid | 10.5 | 8 | 5 | 4.5 | 4 | 4 | 5 | 4 | 4 | 5 | 4 |

Numbers represent the mean of measurements in two batch fermentations.
5 HMF and furfural: g/l, others: ppm

EXAMPLE 5

Identifying a Range of Concentrations of Liquid Fraction From Pretreated Lignocellulosic Biomass that Inhibit *Lactobacillus* Contaminants but do not Substantially Affect Yeast Growth in Glucose Fermentation Fermentation inhibitors are primarily found in the liquid fraction of pretreated lignocellulosic biomass. Accordingly, the following experiments were conducted with dilutions of liquid fraction from wheat straw pretreated under the conditions described in Example 1.

Liquid fraction (pH regulated with acetate and $Na_2CO_3$) was used undiluted (100%), or diluted to 75% full strength, 50%, 25% or 10% using 0.1 M acetate buffer. Initial concentrations of inhibitors corresponding to each of these dilutions were measured by HPLC and are shown in Table 2.

TABLE 2

Initial concentrations of inhibitors corresponding to the dilutions of liquid fraction used in example 5, 6 and 7.

| | 100% | 50% | 25% | 10% |
|---|---|---|---|---|
| 5 HMF [g/l] | 0.19 | 0.13-0.16 | 0.07-0.11 | 0.09 |
| Furfural [g/l] | 0.74 | 0.34-0.38 | 0.19-0.21 | 0.14 |
| 2-furoic acid | 46 | 26-36 | 15-25 | 11 |
| Vanillin | 22 | 10-16 | 8 | 7 |
| Ferulic acid | 35 | 24-41 | 11-22 | 3 |
| Coumaric acid | 16 | 9-17 | 4-8 | 2 |
| Syringic acid | 11 | 8-12 | 4 | 3 |
| Syringaldehyd | 9 | 6-7 | 5-6 | 5 |
| Homovanillic acid | n.d | 4-5 | 3-4 | 3 |
| 4-OH benzaldehyd | 5 | 0-4 | 0-2 | 1 |
| Acetosyringone | 2 | 4-7 | 1-4 | 0 |
| Total phenol cal. | 167 | 101-167 | 60-86 | 42 |
| Acetate [g/l]* | 4.87 | 5.15-4.59 | 4.60-4.62 | 4.63 |

Concentrations are in ppm if nothing else is stated. n.d: not determined
*Acetate was used as buffer - concentration accordingly does not varying much between dilutions Other compounds that might have contributed to the inhibition effects, as for example formic acid and levulinic acid, were not determined. The compounds phenol, guaiacol, syringol, 4-OH benzylalcohol, trimethoxybenzaldehyde, trimethoxyacetophenone, 4-OH acetophenone, acetovanillone, vanillyl alcohol, 4 OH benzoic acid and vanillic acid were found in quite low start concentrations (below 7 ppm in 100% liquid fraction).

*Lactobacillus* were inoculated to different levels in fermentations reported in Examples 5, 6 and 7. These levels are shown in Table 3.

TABLE 3

Inoculation levels of *Lactobacillus* used in examples 5, 6 and 7.

| CFU/ml | Inoculation level | Used in example |
|---|---|---|
| $7*10^8$ to $10^9$ | high | 5 |
| $10^7$ | Low | 6, 7 |

Different inoculation levels were used to demonstrate the inhibition effect in different situations and to further evaluate the effects of inhibitors on *Lactobacillus* growth and lactate production. The "high" inoculation level is not regarded as a realistic contamination level in second generation bioethanol production. Hydrolysis and fermentation in second generation production follow immediately after a lignocellulosic pretreatment step which in all known cases kills bacteria. Realistic conditions are expected to fall closer to the "low" inoculation levels. In first generation bioethanol processes, considered to be much more vulnerable to contamination, contamination levels varied from $10^4$ CFU/ml to $5*10^6$ in wet mill facilities, and from $10^4$ CFU/ml to $5*10^8$ CFU/ml in dry mill facilities. See e.g. ref. 16.

The experiment was conducted at Inbicon laboratories, Fredericia, Denmark. The effects of liquid fraction on glucose fermentation were examined using 6% glucose and different dilutions of liquid fraction. Fermentations were conducted with either yeast or *Lactobacillus*, to identify differences in tolerance to liquid fraction.

Fermentation was conducted using 250 ml blue cap bottles with a membrane cap, equipped with a 1.2 mm sterile needle with a 0.2 μm filter to allow $CO_2$ to escape. The membrane cap further allowed small subsamples to be retrieved with a 2 mm needle without disturbing the anaerobic environment, to determine yeast and *Lactobacillus* CFU, and to conduct HPLC analysis of ethanol and glucose over time. Each treatment was conducted using two replicates (separate flasks). Measurements are means of two replicates. There was no adjustment of pH. The total volume added to each bottle was 80 ml.

Fermentation was conducted at 35° C. Yeast (THERMOSACC™ from Ethanol Technology, $4*10^6$ CFU/ml), and *Lactobacillus* ($7*10^8$ CFU/ml of a mixture of equal amounts of *L. paracasei* P4126 and *L. plantarum* P5868, see ref. 17) was added. Newly harvested *Lactobacillus* from an approximately 36-hour-old culture in MRS bouillon was used as inoculum.

Results are presented in FIGS. 6, 7 and 8. Measurements are means of two replicates. Standard deviation bars are also shown. The different lines labelled 100%, 50% and 25% refer to the different concentrations of liquid fraction. FIG. 6 shows yeast (A) and *Lactobacillus* (B) CFU over the course of fermentation in the presence of different dilutions of liquid fraction. FIG. 7 shows ethanol (A) and lactate (B) concentrations over the course of fermentation in the presence of different dilutions of liquid fraction. FIG. 8 shows glucose concentrations for both yeast and *Lactobacillus* incubations over the course of fermentation in presence of different dilutions of liquid fraction.

As shown in FIG. 6A, yeast grows at the 50% dilution of liquid fraction, but not at 100%. Yeast also did not grow at 75% dilution of liquid fraction (not shown).

As shown in FIG. 7A, yeast ferments ethanol at the 50% dilution of liquid fraction, but not at 100%. Yeast also did not ferment ethanol at 75% dilution of liquid fraction (not shown).

As shown in FIG. 6B, in contrast, even diluted liquid fraction was clearly toxic to *Lactobacillus*. At these very high *Lactobacillus* inoculation levels, cells died rapidly at 100% liquid fraction and at the 50% and 25% dilution.

As shown in FIG. 7B, liquid fraction also inhibited lactate production. At these very high *Lactobacillus* inoculation levels, liquid fraction exhibits a clear concentration-dependent inhibitory effect on lactate production.

As shown in FIG. 8, glucose consumption by *Lactobacillus* was very low at 100% liquid fraction and at the 50% and 25% dilution. This indicates that *Lactobacillus* did not thrive under any of these conditions. In contrast, as also shown in FIG. 8, glucose consumption by yeast was robust, indicating that yeast thrived, at both the 50% and 25% dilution of liquid fraction.

EXAMPLE 6

Dependence of *Lactobacillus* Growth and Lactate Production on Concentration of Liquid Fraction in a Second Generation Bioethanol SSF Process Experiments were conducted at Inbicon laboratories, Fredericia, Denmark. The effects of liquid fraction on a second generation SSF bioethanol process were examined using different dilutions of liquid fraction. SSF of wheat straw pretreated according to the conditions of Example 1 was conducted at dry matter content 9.6% in the presence of different dilutions of liquid fraction. Liquid fraction of steam pretreated wheat straw was prepared as described in Example 5. Three different concentrations of liquid fraction were tested at the "low" level of *Lactobacillus* inoculation.

SSF was conducted using 250 ml blue cap bottles with a membrane cap, equipped with a 1.2 mm sterile needle with a 0.2 μm filter to allow $CO_2$ to escape. The membrane cap further allowed small subsamples to be retrieved without disturbing the anaerobic environment, to determine yeast and *Lactobacillus* CFU, and to conduct HPLC analysis of ethanol and glucose over time. Each treatment was conducted using two replicates (separate flasks). Measurements are means of two replicates. Initial pH was adjusted to 5.0 and maintained between 4.9-5.1 using daily additions of appropriate quantities of 2 M NaOH every day during the experiment. The total volume added to each bottle was 180 ml, which contained pretreated wheat straw sufficient to provide 9.6% dry matter and liquid fraction (pH regulated with acetate and $Na_2CO_3$) diluted with 0.1 M acetate buffer to 50%, 25% or 10%. NOVOZYM 188™ and CELLUCLAST 1.5 FG™ were mixed together in the ratio 1:5 and added at, collectively, 7 FPU/g dry matter for a 6 hours prehydrolysis at 50° C. After 6 hours, the temperature was lowered to 37° C., and yeast (THERMOSACC™ from Ethanol Technology, 3 g/kg dry matter), and *Lactobacillus* were added. *Lactobacillus* was added at a low inoculation level of $10^7$ CFU/ml, which is a more realistic representation of conditions in second generation bioethanol fermentation than the high inoculation level used in Example 5. Newly harvested *Lactobacillus* from an approximately 36-hour-old culture in MRS bouillon was used as inoculum, having a mixture of equal amounts of *L. paracasei* P4126 and *L. plantarum* P5868, see ref. 17)

Results are presented in FIGS. 9 and 10. Measurements are means of two replicates. Standard deviation bars are also shown. The different lines labelled 50%, 25% and 10% refer to the different concentrations of liquid fraction. FIG. 9 shows yeast and *Lactobacillus* CFU during the course of fermentation at different dilutions of liquid fraction. FIG. 10 shows ethanol and lactate concentrations during the course of fermentation at different dilutions of liquid fraction. The time point t=0 represents the start of fermentation.

As shown in FIG. 9, at these low levels of *Lactobacillus* inoculation, the 50% dilution of liquid fraction effectively completely inhibited *Lactobacillus* growth. The 25% dilution of liquid fraction also provided substantial inhibition of *Lactobacillus* growth. In contrast, as shown, neither the 50% nor the 25% dilution of liquid fractions affected final yield.

As shown in FIG. 10, at these low levels of *Lactobacillus* inoculation, under the conditions of fermentation at 9.6% dry matter, bacterial lactate production remained beneath 2 g/kg, even at the 10% dilution of liquid fraction. It should be noted that in industrial fermentation processes, much higher dry matter content would likely be used, which would be expected to result in higher levels of lactate production. The 25% and 50% dilutions of liquid fraction clearly substantially inhibited bacterial lactate production. In contrast, in all of the dilutions of liquid fraction tested, 50%, 25% and 10%, final ethanol yields were not affected.

EXAMPLE 7

Dependence of *Lactobacillus* Lactate Production on Concentration of Liquid Fraction in a First Generation Bioethanol Fermentation Experiments were conducted at Inbicon laboratories, Fredericia, Denmark. The effects of liquid fraction on a first generation SSF bioethanol process were examined using different dilutions of liquid fraction. SSF of hydrolysed wheat flour was conducted at dry matter content 10% in the presence of different dilutions of liquid fraction. Liquid fraction of steam pretreated wheat straw was prepared as described in Example 5. Three different concentrations of liquid fraction were tested at the "low" level of *Lactobacillus* inoculation.

SSF was conducted using 250 ml blue cap bottles with a membrane cap, as described in Examples 5 and 6. Each treatment was conducted using two replicates (separate flasks). Measurements are means of two replicates. Initial pH was adjusted to 5.0 and maintained between 4.9-5.1 using daily additions of appropriate quantities of 2 M NaOH every day during the experiment. Hydrolysis was first conducted at 18% dry matter content by mixing flour and 0.1 M acetate buffer with NS50033 (Novozymes, 14 g/kg flour). Flasks were incubated at 50° C. for 22 hours. After 22 hours, liquid fraction (pH regulated with acetate and $Na_2CO_3$) and 0.1 M acetate buffer was added in various amounts. The total volume added to each bottle was 180 ml, which contained hydrolysed wheat flour and liquid fraction diluted to 50%, 25% or 10% of full strength or a buffer control, 0%. The temperature was lowered to 37° C. Yeast (THERMOSACC™ from Ethanol Technology, 3 g/kg dry matter), and *Lactobacillus* were added. *Lactobacillus* was added at a low inoculation level of $10^7$ CFU/ml, as described in Example 6.

Results are shown in FIG. 11, which shows ethanol and lactate concentrations during the course of fermenation at different dilutions of liquid fraction. The time point t=0 is start of fermentation. Measurements are means of two replicates. Standard deviation bars are also shown. The different lines labelled 50%, 25% and 0% refer to the different concentrations of liquid fraction.

As shown in FIG. 11, the first generation process is fast compared to the second generation process described in example 6. The first generation process is generally more vulnerable towards *Lactobacillus* contamination. This is indicated by the high lactate concentrations obtained with low *Lactobacillus* inoculation ($10^7$ CFU/ml), resulting in up to 15 g/l in the first generation process, compared to a maximum of about 2 g/l in the second generation process, using a roughly comparable quantity of theoretically fermentable sugars.

As shown, the 50% dilution of liquid fraction proved totally effective in suppressing *Lactobacillus* lactate production. In contrast, as shown, the 50% dilution did not affect yeast ethanol production.

EXAMPLE 8

Non-Sterile Fermentation of Pretreated Wheat Straw Having Water/Biomass Ratio 5:1 and Further Diluted with Water or Supplemented with Liquid Fraction Experiments were conducted at the IBUS pilot plant of Inbicon in Fredericia, Denmark. Cut wheat straw (average particle size of approximately 40 mm), 50 kg/hour having 92.0% initial non-water content, was continuously pretreated by steam at 185-200° C. for 10-15 minutes. The pretreated wheat straw was subject to a secondary pretreatment consisting of a washing and pressing step. The pretreated wheat straw was washed by water in such manner as to achieve a water/biomass ratio of 5:1 in pretreatment and post-pretreatment processing.

After washing and pressing, the fiber fraction comprised insoluble fibres and had a dry matter content of approximately 35%. Inhibitor concentrations were measured by HPLC (not shown). Alternatively water or liquid fraction was added to the fiber fraction in various amounts, to obtain a dry matter content of 26%, and to achieve inhibitor concentrations roughly approximating those observed with the 50% and 25% dilution of liquid fraction described in examples 5, 6 and 7.

Other compounds that might have contributed to the inhibition effects, as for example formic acid and levulinic acid, were not determined. The compounds phenol, guaiacol, syringol, 4-OH benzylalcohol, trimethoxybenzaldehyd, trimethoxyacetophenone, acetovanillone, vanillyl alcohol, and 4 OH benzoic acid were found in quite low start concentrations (below 3 ppm).

Fibers were pre-hydrolysed by means of addition of NOVOZYME 188™ and CELLUCLAST 1.5 FG™ at 50° C. To the pre-hydrolysed fiber fraction, yeast was added (THERMOSACC™, 3 g/kg DM, obtained from Ethanol Technology), and *Lactobacillus* at the low level, as described in Examples 5 and 6. The fermentation mixture was simultaneously saccharified and fermented (SSF) at 37° C. The SSF was conducted in a non-sterile free fall mixer, according to the process described by WO2006/056838.

Results are shown in FIGS. 12 and 13. The different lines labelled 50% and 25% refer to the different levels of inhibitor dilution. FIG. 12 shows *Lactobacillus* CFU over the course of the SSF process at different levels of inhibitor dilution. FIG. 13 shows ethanol (A) and lactate (B) concentrations over the course of the SSF process at different levels of inhibitor dilution.

As shown, even where *Lactobacillus* has been actively added to the fermentation mixture, contaminating bacterial growth and lactate production were suppressed while ethanol production was substantially unaffected.

The examples and descriptions provide representative examples of particular embodiments and are not intended to limit the scope of the invention as defined by the claims.

REFERENCES

1 H. Klinke et al., "Inhibition of ethanol-producing yeast and bacteria by degradation products produced during pretreatment of biomass," Appl. Microbiol. Biotechnol. (2004) 66:10.

2 C. Martin et al., "A study of three strategies for improving the fermentability of sugarcane bagasse hydrolysates for fuel ethanol production," International Sugar Journal (2007) 109(1297):33

3 S. Shinsuke et al., "Effect of lignocellulose-derived inhibitors on growth of and ethanol production by growth-arrested *Corynebacterium glutamicum* R," Applied and Environmental Microbiology (2007) 73(7):2349

4 WO2006/032282

5 D. Schell et al., "Contaminant occurrence, identification and control in a pilot-scale corn fiber to ethanol conversion process," Bioresource Technology (2007) 98: 2942

6 N. Mosier et al., "Features of promising technologies for pretreatment of lignocellulosic biomass," Bioresource Technology (2005) 96:673

7 Palmquist E, H Grage, N Q Meinander and B Hahn-Hägerdal (1999). Main and interaction effects of acetic acid, furfural, and p-hydroxybenzoic acid on growth and ethanol productivity of yeasts. Biotechnol. Bioeng. 63: 46-55

8 Zaldivar J, A Martinez and L O Ingram (1999). Effects of selected aldehydes on the growth and fermentation of ethanologenic *Escherichia coli*. Biotechnol. Bioeng. 65. 24-33

9 N. Ariz, et al., "Comparative antibacterial and antifungal effects of some phenolic compounds," Microbios (1998) 374:43

10 R. Capasso et al., "Antibacterial polyphenols from olive oil mill waste waters," Journal of Applied Bacteriology (1995) 79:393

11 S. Naz et al., "Antibacterial activity directed isolation of compounds from *Onosma hispidum*," Microbiological Research (2006) 161:43

12 M. Fernandez et al., "Antibacterial activity of the phenolic acids fractions of *Scrophularia frutescens* and *Scrophularia sambucifolia*," Journal of Ethnopharmacology (1996) 53:11

13 M. Mokbel and T. Suganuma, "Antioxidant and antimicrobial activities of the methanol extracts from pummelo (*Citrus grandis* Osbeck) fruit albedo tissues," Eur. Food Res. Technol (2006), 224:39

14 Almeida J R M, T Modig, A. Petersson, B. Hähn-Hägerdal, G. Lidén and M F Gorwa-Grauslund (2007). Increased tolerance and conversion . . . Journal of chemical technology and biotechnology 82: 340-349

15 Liu Z L. (2006) Genomic adaptation of ethanologenic yeast to biomass conversion inhibitors. Appl Microbiol Biotechnol 73: 27-36

16 Skinner K. A. & T. D. Leathers (2004). Bacterial contaminants of fuel ethanol production. J Ind Microbiol Biotechnol, vol 31, pp 401-408

17 Thomsen M H, Kiel P (2008) Selection of lactic Acid Bacteria for Acidification of Brown juice (grass juice) with the aim of making a durable substrate for L-lysine fermentation. Journal of the Science of Food and Agriculture. 88: 976-983.

The invention claimed is:

1. A method of yeast fermentation of starch biomass comprising the steps of:
   preparing a non-sterile yeast fermentation mixture comprising primarily starch biomass and optimized levels of fermentation inhibitors that inhibit contaminating bacterial growth and/or lactate production while having substantially no effect on ethanol fermentive yeast, and fermenting said fermentation mixture,
   wherein optimized levels of fermentation inhibitors are achieved by addition of isolated and/or concentrated extracts from liquid fraction or wash waters of pretreated lignocellulosic biomass.

2. The method of claim 1 wherein the extracts comprise a portion of liquid fraction remaining after useful C5 sugars have been removed.

3. The method of claim 1 wherein the extracts comprise a portion of liquid fraction remaining after useful C5 sugars have been removed and extracts have been concentrated to a concentrated liquid.

4. The method of claim 1 wherein the extracts comprise a portion of liquid fraction remaining after hazardous or unwanted materials have been removed.

5. The method of claim 1 wherein the extracts comprise a portion of liquid fraction remaining after hazardous or unwanted materials have been removed and extracts have been concentrated to a concentrated liquid.

6. The method of claim 1 wherein the extracts are derived from liquid fraction or wash waters from steam pretreated corn stover, wheat straw or bagasse.

7. The method of claim 1 wherein said lignocellulosic biomass is pretreated to a severity index of at least 3.0.

* * * * *